US00PP29595P3

(12) United States Plant Patent
Hogenboom

(10) Patent No.: US PP29,595 P3
(45) Date of Patent: Aug. 14, 2018

(54) ***PHLOX* PLANT NAMED 'HOG1701'**

(50) Latin Name: *Phlox paniculata*
Varietal Denomination: HOG1701

(71) Applicant: Hogenboom Phloxen, Roelofarendsveen (NL)

(72) Inventor: Jeroen Hogenboom, Roelofarendsveen (NL)

(73) Assignee: Hogenboom Phloxen, Roelofarendsveen (NL)

( * ) Notice: Subject to any disclaimer, the term of this patent is extended or adjusted under 35 U.S.C. 154(b) by 0 days.

(21) Appl. No.: 15/731,779

(22) Filed: Sep. 25, 2017

(65) Prior Publication Data

US 2018/0035595 P1 Feb. 1, 2018

(51) Int. Cl.
*A01H 5/02* (2018.01)

(52) U.S. Cl.
USPC ..... Plt./320
CPC ..... *A01H 5/02* (2013.01)

(58) Field of Classification Search
USPC ..... Plt./320
See application file for complete search history.

(56) References Cited

PUBLICATIONS

PLUTO Plant Variety Database May 5, 2018. p. 1.*

* cited by examiner

*Primary Examiner* — Annette H Para
(74) *Attorney, Agent, or Firm* — Samuel R. McCoy, Jr.

(57) ABSTRACT

'HOG1701' is a new and distinctive variety of *Phlox* plant which is characterized by a relatively slow rate of growth and bright white flowers. The new variety propagates successfully by stem cuttings and has shown to be uniform and stable in the resulting generations from asexual propagation.

3 Drawing Sheets

Latin name of the genus and species: The Latin name of the genus and species of the novel variety disclosed herein is *Phlox paniculata.*

Variety denomination: The inventive variety of *Phlox* disclosed herein has been given the variety denomination 'HOG1701'.

CROSS REFERENCE TO RELATED APPLICATIONS

This application claims priority to the Netherlands Plant Breeders Rights application number VBL216, filed Jul. 31, 2016, which is herein incorporated by reference.

BACKGROUND OF THE INVENTION

Parentage: 'HOG1701' is a seedling selection resulting from the controlled pollination of an emasculated *Phlox paniculata* 'Crissy' plant (not patented in the United States; Netherlands PBR grant number 33669), the seed parent, with *Phlox paniculata* 'Danielle' (not patented), the pollen parent, at a commercial nursery in Roelofarendsveen, Netherlands, in June of 2011. Seed from said cross was harvested, then germinated, and the resulting seedlings were grown to a mature size in order to evaluate for desirable commercial characteristics. In approximately July of 2012, the inventor selected the new *Phlox* cultivar due to its slower rate of growth and bright white flower. This new and distinctive cultivar was given the name 'HOG1701'.

Asexual Reproduction: Asexual reproduction of 'HOG1701' was first accomplished in August of 2012 by rooting softwood stem cuttings at a commercial greenhouse in Roelofarendsveen, Netherlands. Eight successive generations have shown that the unique features of the instant cultivar are stable and reproduce true to type.

SUMMARY OF THE INVENTION

The cultivar 'HOG1701' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Phlox* cultivar, 'HOG1701'.

1. *Phlox* 'HOG1701' exhibits a slow rate of growth; and
2. *Phlox* 'HOG1701' exhibits bright white flowers.

BOTANICAL DESCRIPTION OF THE PLANT

Figure 1:
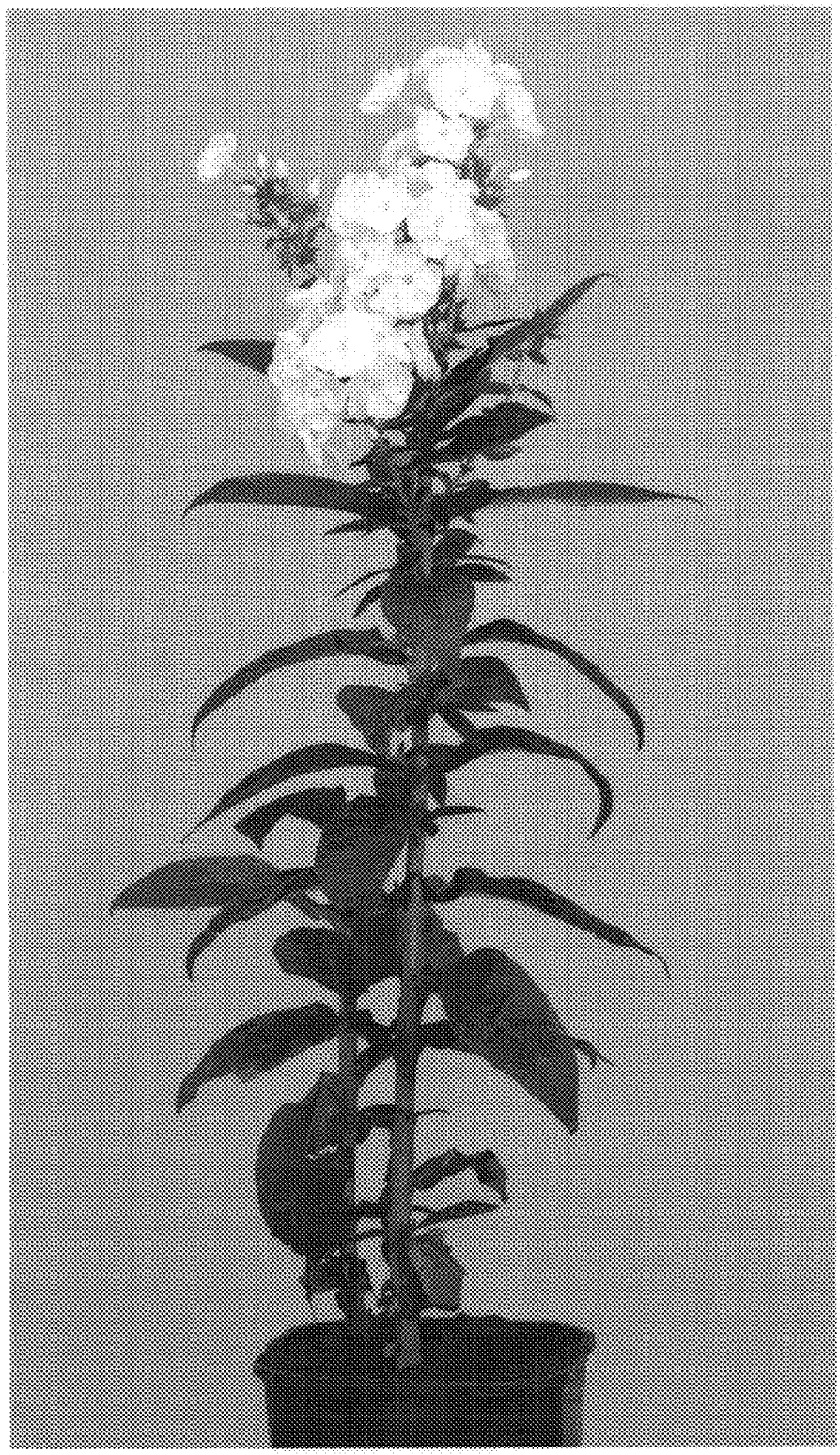
FIG. 1 shows, as nearly true as it is reasonably possible to make the same in color illustrations of this type, an exemplary 'HOG1701' plant at approximately 12 month old, potted into a 13 cm nursery container, grown outdoors in Roelofarendsveen, Netherlands.
Figure 2:
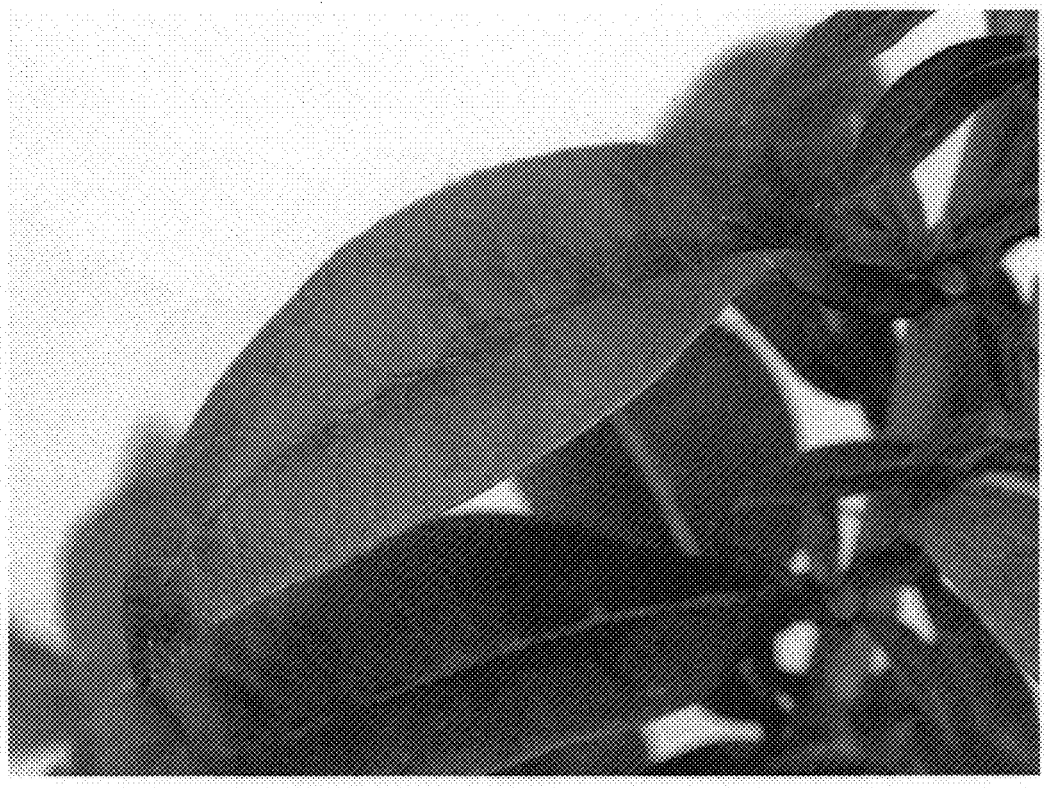
FIG. 2 shows, as nearly true as it is reasonably possible to make the same in color illustrations of this type, the typical foliage of the plant in FIG. 1.
Figure 3:
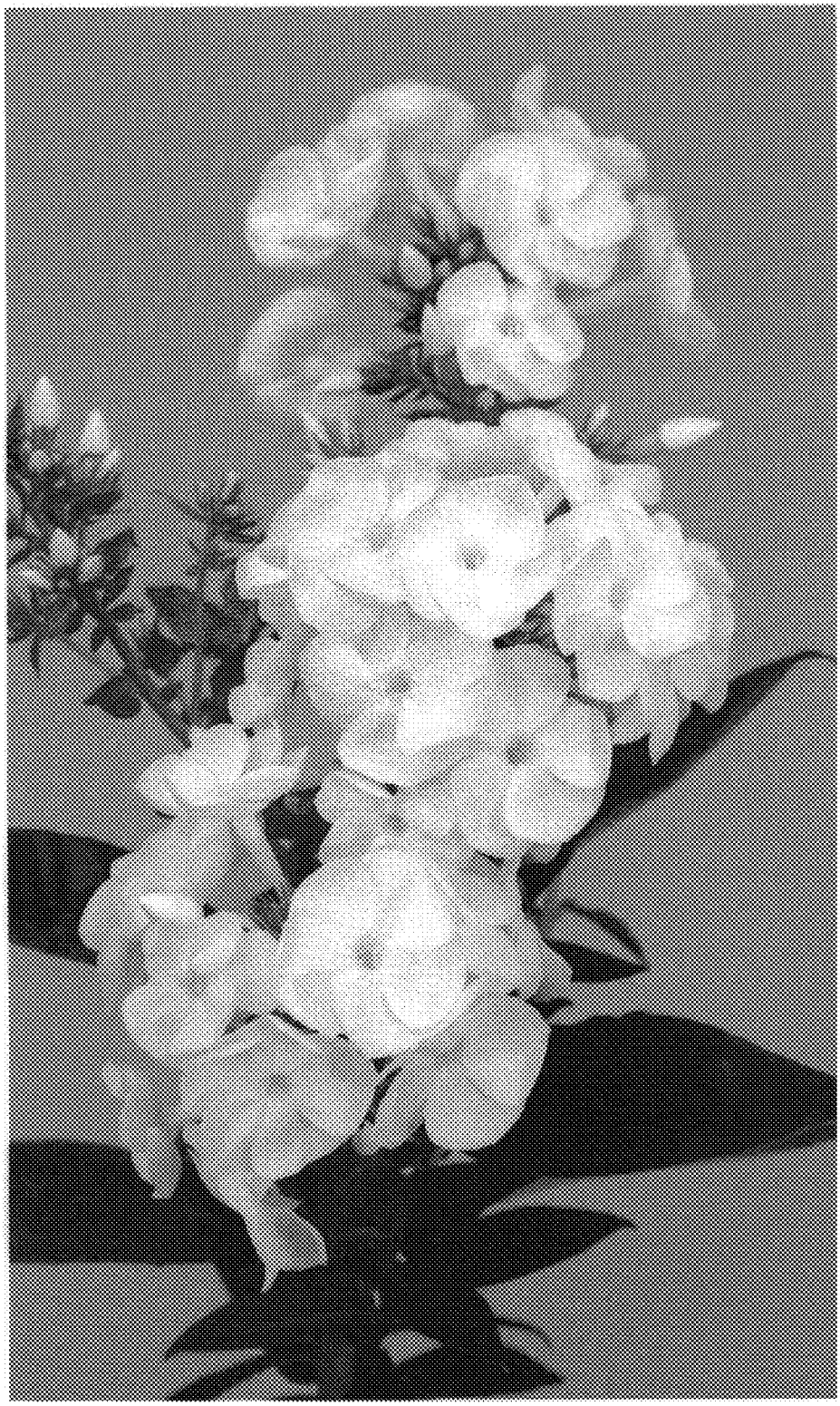
FIG. 3 shows, as nearly true as it is reasonably possible to make the same in color illustrations of this type, the typical inflorescence of the plant in FIG. 1.

The following observations and measurements were made in August of 2017 and describe averages from a sample set of six specimens of 12 month old 'HOG1701' plants grown in 13 cm nursery containers grown outdoors in Roelofarendsveen, Netherlands. Plants were produced using conventional field-grown production protocols for *Phlox* which consisted of regular fertilizer applications and natural rainfall, supplemented with drip irrigation as required. Pest or disease control measures were utilized in production as required. Plants were produced with full sun exposure and no photoperiodic treatments or artificial light was given to the plants.

Those skilled in the art will appreciate that certain characteristics will vary with older or, conversely, with younger plants. 'HOG1701' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'HOG1701' and a comparison with the parent plants and most similar variety of *Phlox* are provided below.

General plant description:

*Growth habit*.—Herbaceous perennial; narrowly upright.

*Plant form*.—Narrow obovate.

*Average height*.—53.7 cm, from the soil level to the top of the foliar plane, and 63.4 to the top of the floral plane.

*Plant spread*.—Average of 35.3 cm.

*Growth rate*.—Moderate to high.

*Plant vigor*.—High.

*Propagation type*.—Softwood stem cuttings.

*Time to initiate roots*.—Approximately 14 days to initiate roots at 22 degrees Celsius.

*Time to produce a finished plant*.—Approximately 12 months are needed to produce a marketable plant in an 8 cm container.

*Pest resistance and susceptibility*.—Not any more or less tolerant or susceptible to pests or diseases known to effect *Phlox*.

*Temperature tolerances*.—USDA Zones 6 to 10; at least tolerant of temperatures ranging from minus 20 degrees Celsius to 35 degrees Celsius. Moderate tolerance to rain inundation; high tolerance to wind.

Root system:

*General*.—Moderately fibrous; freely branched; moderately dense.

*Distribution in the soil profile*.—Shallow.

*Diameter of primary roots*.—0.2 cm.

*Color*.—Yellow-white, nearest to a combination of RHS 158B and 158C.

*Texture*.—Smooth, with no root hairs.

Stem:

*Branching habit*.—Main stems with no lateral branching. Pinching isn't required but may improve branching.

*Number of main stems per plant*.—An average of 2 main stems.

*Number of lateral branches per plant*.—0.

*Appearance; cross-section*.—Rounded.

*Length of lateral branches*.—53.2 cm.

*Diameter of lateral branches*.—0.8 cm.

*Internode length on lateral branches*.—3.0 cm.

*Aspect*.—Approximately 10 degrees from vertical.

*Strength*.—Very strong.

*Color, juvenile*.—Yellow-green, nearest to RHS 145A.

*Color, mature*.—Yellow-green, nearest to a combination of RHS 144A and 144B.

*Color at internodes*.—Yellow-green, nearest to a combination of RHS 144A and 144B.

*Texture and luster*.—Glabrous and slightly glossy.

Foliage:

*Arrangement*.—Opposite.

*Attachment*.—Petiolate.

*Division*.—Simple.

*Quantity of leaves*.—36.

*Petioles*.—Length — 0.4 cm. Diameter — Petiole flattened; average width is 0.3 cm and average height is 0.2 cm high. Strength — Strong. Texture and luster, adaxial surface — Glabrous, smooth, and slightly glossy. Texture and luster, abaxial surface — Glabrous, smooth, and slightly glossy. Color, adaxial surface — Yellow-green, nearest to RHS 144B. Color, abaxial surface — Yellow-green, nearest to in between RHS 144C and 145A.

*Lamina*.—Dimensions — 12.9 cm long and 4.9 cm wide. Shape of blade — Elliptic to ovate and narrow ovate. Attitude — At an angle of approximately 30 degrees to the main stem. Aspect — Reflexed. Apex — Apiculate. Base — Truncate. Margin — Entire; slightly undulated. Pubescence, texture and luster of adaxial surface — Glabrous, slightly rugose, and very slightly glossy. Pubescence, texture and luster of abaxial surface — Glabrous, slightly rugose, and matte. Color — Juvenile foliage, adaxial surface — Green, nearest to RHS 143B. Juvenile foliage, abaxial surface — Green, nearest to RHS 143C. Mature foliage, adaxial surface — Green, nearest to RHS NN137A. Mature foliage, abaxial surface — Yellow-green, nearest to RHS 147B. Venation — Pattern — Pinnate. Mature foliage venation, adaxial surface — Yellow-green, nearest to RHS 145A. Mature foliage venation, abaxial surface — Yellow-green, nearest to RHS 145A.

Inflorescence:

*Type*.—Panicle.

*Natural flowering season*.—Summer to late summer in Roelofarendsveen, Netherlands.

*Time to flower*.—Approximately 10 months.

*Dimensions*.—26.0 cm high, not including peduncle, and 17.8 cm in diameter.

*Abundance of inflorescence*.—Approximately 4 inflorescence per plant.

*Quantity of open flowers per plant*.—Approximately 35.

*Quantity of buds per plants*.—Approximately 445.

*Attitude*.—Upright.

*Peduncles*.—Length — Average of 14.6 cm. Diameter — Average of 0.4 cm. Attitude — Upright; approximately 10 degrees from vertical. Strength — Very strong. Texture — Smooth; glabrous. Luster — Moderately glossy. Color — Yellow-green, nearest to in between RHS 144A and 144B.

Flower buds:

*Shape*.—Elliptic.

*Dimensions*.—1.5 cm long and 0.6 cm in diameter.

*Texture*.—Smooth; glabrous.

*Luster*.—Matte.

*Color*.—The distal half of the bud is green-white, nearest to RHS 157D, and the proximal half of the bud is green, nearest to RHS 143D.

Flower:

*Flowering habit*.—Freely flowering.

*Shape*.—Salverform.

*Flower depth*.—2.9 cm.

*Flower diameter*.—3.4 cm.

*Diameter of floral throat*.—0.4 cm.

*Floral throat texture*.—Glabrous; moderately velvety.

*Diameter of floral tube*.—0.3 cm.

*Length of floral tube*.—2.2 cm.

*Floral tube texture*.—Moderately covered with very short hairs; hairs with an average length of 0.03 cm and colored green-white, nearest to RHS 157D.

*Aspect*.—Flowers are outward facing.

*Fragrance*.—Moderately to strongly fragrant; sweet and very pleasant, typical of *Phlox paniculata*.

*Lastingness*.—Approximately 10 days.

*Persistent*.—Self-cleaning.

*Pedicels*.—Dimensions — 0.3 cm long and 0.1 cm in diameter. Attitude — At an average angle of 60 degrees to the peduncle. Strength — Medium. Texture and luster — Glabrous, smooth and moderately glossy. Color — Yellow-green, nearest to RHS 144C.

*Petals*.—Quantity of Petals — 5. Arrangement — Single whorl; petals are rotate and fused into an elongated tube at the base; lower 57.5 percent of the petals are fused; free portion of the petals are moderately to strongly overlapping. Shape of petal lobes — Spatulate. Dimensions, free portion of petals — 3.8 cm long and 2.2 cm wide. Apex — Obtuse. Base — Fused into a tube. Margin — Entire; lightly undulated. Aspect — Cupped. Pubescence, texture and luster of upper surface — Glabrous, velvety and very slightly glossy. Pubescence, texture and luster of lower surface — Glabrous, velvety and very slightly glossy. Petal lobe color when opening, upper surface — White, nearest to in between RHS NN155C and NN155D. Petal lobe color when opening, lower surface — White, nearest to in between RHS NN155C and NN155D. Petal lobe color when fully opened, upper surface — White, nearest to in between RHS NN155C and NN155D; not fading. Petal lobe color when fully opened, lower surface — White, nearest to in between RHS NN155C and NN155D; not fading. Petal venation when fully opened, upper surface — White, nearest to in between RHS NN155C and NN155D. Petal venation when fully opened, lower surface — White, nearest to in between RHS NN155C and NN155D. Floral throat color — Green-white, nearest to RHS 157D; RHS 150D when opening. Floral throat venation color — Green-white, nearest to RHS 157D; RHS 150D when opening. Floral tube color, when fully opened — White, nearest to RHS 155C. Floral tube venation color — White, nearest to RHS 155C.

*Calyx*.—Shape — Rotate. Dimensions — 0.8 cm in diameter and 0.3 cm tall. Sepals — Arrangement — Rotate; lower 12.5% is fused. Quantity — 5. Shape — Lanceolate. Sepal dimensions — 0.8 cm long and 0.2 cm wide. Apex — Narrow apiculate. Base — Cuneate. Margin — Entire; not undulated. Texture and luster, upper surface — Glabrous, smooth, and slightly glossy. Texture and luster, lower surface — Glabrous, smooth, and slightly glossy. Color when opening, upper surface — Yellow-green, nearest to RHS 144B, and margined lighter, nearest to RHS 145D. Color when opening, lower surface — Yellow-green, nearest to RHS 144B, and margined lighter, nearest to RHS 145D. Color when fully opened, upper surface — Yellow-green, nearest to RHS 144B, and margined lighter, nearest to RHS 145D. Color when fully opened, lower surface — Yellow-green, nearest to RHS 144B, and margined lighter, nearest to RHS 145D. Sepal venation when fully opened, upper surface — Yellow-green, nearest to RHS 144B, and margined lighter, nearest to RHS 145D. Sepal venation when fully opened, lower surface — Yellow-green, nearest to RHS 144B, and margined lighter, nearest to RHS 145D.

Reproductive organs:

*Androecium*.—Stamen quantity — 5. Filament length — 0.1 cm. Filament color — White, nearest to in between RHS 155A and 155B. Anther shape — Narrow oblong. Anther length — 0.25 cm. Anther width — 0.1 cm. Anther color — White, nearest to RHS 155A. Pollen, presence — Moderately abundant. Pollen, color — Greyed-yellow, nearest to RHS 160D.

*Gynoecium*.—Pistil quantity — 1. Pistil length — 1.5 cm. Style length — 1.4 cm. Style color — Yellow-green, nearest to RHS 144C. Stigma shape — Cleft; three-parted. Stigma length — 0.1 cm. Stigma diameter — 0.15 cm. Stigma color — Yellow-green, nearest to RHS N144B. Ovary color — Green, nearest to RHS 143B.

Seed and fruit: None observed.

Comparisons with the Parent Plants and Most Similar Variety of Common Knowledge Plants of the new cultivar 'HOG1701' differ from its seed parent, *Phlox paniculata* 'Crissy' plant (not patented in the United States; Netherlands PBR grant number 33669), by the characteristics described in Chart 1.

CHART 1

| Characteristic | 'HOG1701' | 'Crissy' |
|---|---|---|
| General coloration of the flower. | White. | Purple. |

Plants of the new cultivar 'HOG1701' differ from its pollen parent, *Phlox paniculata* 'Danielle' (not patented), by the characteristics described in Chart 2.

CHART 2

| Characteristic | 'HOG1701' | 'Danielle' |
|---|---|---|
| Rate of growth. | Faster slower than 'Danielle'. | Slower faster than 'HOG1701'. |
| Leaf shape. | Leaves are more flat. | Leaves are more rounded. |
| Leaf apex. | Less pointed. | More pointed. |

Plants of the new cultivar 'HOG1701' may be distinguished from its most similar known commercial comparator, *Phlox* 'Dasfive' (not patented in the United States; NL Plant Breeders Rights grant number 15635), by the characteristics described in Chart 3.

CHART 3

| Characteristic | 'HOG1701' | 'Dasfive' |
|---|---|---|
| Rate of growth. | Faster growing than 'Dasfive'. | Slower growing than 'HOG1701'. |
| Diameter of lateral branches. | Thicker than 'Dasfive'. | Thinner than 'HOG1701'. |

CHART 3-continued

| Characteristic | 'HOG1701' | 'Dasfive' |
|---|---|---|
| Leaf size. | Larger than 'Dasfive'. | Smaller than 'HOG1701'. |
| Flower size. | Larger than 'Dasfive'. | Smaller than 'HOG1701'. |

That which is claimed is:

1. A new and distinct variety of *Phlox paniculata* plant named 'HOG1701', substantially as described and illustrated herein.

* * * * *